United States Patent [19]

Zimmermann et al.

[11] Patent Number: 5,723,661
[45] Date of Patent: Mar. 3, 1998

[54] PROCESS FOR PREPARING CALCIUM PYRUVATE AND ITS HYDRATES

[75] Inventors: Curt Zimmermann, Mauthausen; Kurt Weissenböck, Enns, both of Austria

[73] Assignee: DSM Chemie Linz GmbH, Linz, Austria

[21] Appl. No.: 814,410

[22] Filed: Mar. 11, 1997

[30] Foreign Application Priority Data

Mar. 11, 1996 [AT] Austria ................... A448/96

[51] Int. Cl.$^6$ ................... C07C 59/19
[52] U.S. Cl. ................... 562/577
[58] Field of Search ................... 562/577

[56] References Cited

U.S. PATENT DOCUMENTS 4,076,745   2/1978   Lodewyk ................... 562/577

FOREIGN PATENT DOCUMENTS 1465432   1/1967   France.

Primary Examiner—Gary Geist
Assistant Examiner—Rosalynd Keys
Attorney, Agent, or Firm—Wenderoth, Lind & Ponack

[57] ABSTRACT

A process for preparing high-purity calcium pyruvate or its hydrates by reacting an aqueous solution of pyruvic acid with an inorganic calcium compound with the pH being set to 2 to 7, preferably 2.5 to 4, which comprises reacting an up to 10% strength aqueous solution of pyruvic acid with the calcium compound, in the presence or absence of a stabilizer or complexing agent, and mixing the resulting solution with an organic diluent at temperatures of 0° to 30° C. and isolating the resulting precipitate of calcium pyruvate or its hydrate from the solution.

7 Claims, No Drawings

PROCESS FOR PREPARING CALCIUM PYRUVATE AND ITS HYDRATES

Calcium pyruvate is used as an additive in the food and drink industry and is prepared starting from pyruvic acid.

French Patent 1,465,432 describes a process, for example, in which calcium carbonate is added to an approximately 13% strength aqueous solution of pyruvic acid and the reaction mixture is heated for some minutes and then cooled, whereupon a precipitate sediments out. Ethanol is then added to the supernatant solution at 95° C., whereupon, after cooling, calcium pyruvate precipitates out, which is filtered off and washed with ethanol. The disadvantage in this process is, as has been shown by a comparison experiment, that the resulting product for the most part comprises cyclic dimers and oligomers of pyruvic acid, the desired monomer only being obtained in a yield of a few percent after separating off the dimers and oligomers.

The object of the present invention was therefore to find a process which, starting from pyruvic acid, gives calcium pyruvate in a simple manner and in high purity, in particular having a very low content of down to less than 0.1% of dimers and oligomers.

Unexpectedly, this object could be achieved by the process of the invention.

The present invention therefore relates to a process for preparing high-purity calcium pyruvate or its hydrates by reacting an aqueous solution of pyruvic acid with an inorganic calcium compound with the pH being set to 2 to 7, preferably 2.5 to 4, which comprises reacting an up to 10% strength aqueous solution of pyruvic acid with the calcium compound, in the presence or absence of a stabilizer or complexing agent, and mixing the resulting solution with an organic diluent at temperatures of 0° to 30° C. and isolating the resulting precipitate of calcium pyruvate or its hydrate from the solution.

In the process of the invention, pyruvic acid is dissolved in enough water to give an up to 10% strength solution. Preferably, a 1 to 8% strength, particularly preferably a 3 to 6% strength, solution is prepared. A calcium compound is then added to this solution, preferably with stirring.

Suitable calcium compounds are inorganic calcium compounds such as calcium carbonate, calcium hydroxide, etc. Preferably, calcium carbonate is used. The calcium compound is added here in an equivalent amount, ie. half a mole of calcium compound per mole of pyruvic acid. Preferably, however, a slight excess of pyruvic acid is used.

Owing to the addition of the calcium compound, a pH of about 2 to 7 is established, preferably of 2.5 to 4.

The reaction temperature is approximately about 0° C. to 60° C., preferably 10° to 40° C., particularly preferably 20° to 30° C.

At the beginning of the reaction, if desired, a conventional complexing agent such as, for instance, ethylenediaminetetraacetic acid (EDTA) or its salts can be added, as a result of which heavy metal traces such as, for instance, iron traces, which are introduced when calcium compounds are used, in particular calcium carbonate, are masked.

An organic acid, preferably an organic acid which is also suitable as a food additive, can also be used as stabilizer, which ensures a pH below 7 during the preparation process and in part likewise masks heavy metal traces. Suitable acids are, for example, citric acid, ascorbic acid, tartaric acid, malic acid, fumaric acid, oxalic acid, etc. Preferably, citric acid is used as additive.

The amount of stabilizer or complexing agent added is preferably between 0.001 and 10 mol %, particularly preferably 0.1 to 5 mol %, based on pyruvic acid.

The clear colorless solution thus obtained is then mixed with an organic diluent. Preferably, a low-boiling highly water-miscible, organic diluent is used here. Examples of suitable diluents are ketches, such as acetone, ethyl methyl ketone etc., alcohols, such as, for instance, ethanol, methanol etc., ethers, such as, for instance, 1,4-dioxane etc. or esters etc. Preferably, ethanol or acetone is used, particularly preferably acetone.

The reaction temperature here is about 0° to 30°, preferably about 5° to 15° C.

The calcium pyruvate precipitate sedimenting out in this process is then freed from diluent, for example by filtration, centrifugation, decanting, then, preferably, washed with the diluent used for the precipitation, and in turn freed from the diluent, for instance by centrifugation, decanting, filtration with suction etc. The moist product is then, for example, freeze-dried or dried in conventional driers at atmospheric pressure or in vacuo. Preferably, the drying is performed in vacuo. The temperatures in the vacuum drying are preferably below 100° C., particularly preferably between 30° and 60° C.

The water content of the calcium pyruvate obtained varies as a function of the drying conditions.

The resulting calcium pyruvate or its hydrates are obtained in high yields and in high purity by the process of the invention. The dimer content in the calcium pyruvate monohydrate prepared according to the invention is down to less than 0.1% (HPLC); trimers and higher oligomers are no longer detectable.

EXAMPLE 1

45 g (0.5 mol) of pyruvic acid (98%) were dissolved in 880 g of deionized water and adjusted to pH 3.5 in the course of 10 minutes, with stirring, with 23 g (0.23 mol) of calcium carbonate. The resulting clear colorless solution was mixed with 2000 ml of cold acetone in the course of 15 minutes with stirring. The resulting white precipitate was freed from solvent by centrifugation, washed with acetone and again centrifuged. The product thus obtained had a dimer content of 0.1% (HPLC, UV determination 204 nm). Trimers or higher oligomers or polymers were not detectable. After drying for 4 h in vacuo at 40° C., 52 g of a pure white product having a content of 98% calcium pyruvate monohydrate were obtained. This corresponds to a yield of 88%, based on pyruvic acid.

Comparison Example: By analogy with FR-B 1,465,432

27 g (0.3 mol) of pyruvic acid (98%) were dissolved in 200 g of deionized water and 16.5 g (0.165 mol) of calcium carbonate were added carefully with stirring. A thick, scarcely stirrable pulpy mass resulted, which converts on heating into a yellow-reddish hazy liquid. After cooling, a precipitate formed. The supernatant solution was decanted and mixed with 600 ml of ethanol at 95° C. The resulting precipitate was filtered off with suction and washed with 50 ml of ethanol. From 71 g of moist product, after drying in vacuo, 28 g of a product were obtained which, according to HPLC analysis, comprised only 4% by weight of calcium pyruvate. The major constituent was open and cyclic dimers and oligomers of pyruvic acid salts, and also water.

18.4 g of this product were dissolved in 100 ml of hot water and freed from small amounts of insoluble contents by filtration. After addition of acetone a precipitate sedimented out, which was filtered, washed with acetone and dried in vacuo. Analysis of the resulting product showed a still lower calcium pyruvate content, in comparison with the uncrystallized product, and a correspondingly high oligomer content.

EXAMPLE 2

Increasing the stability and product quality by adding stabilizers 4.5 g (0.05 mol) of pyruvic acid (98%) were dissolved in 88 g of deionized water and 2 g (0.02 mol) of calcium carbonate were added. The clear solution thus obtained was added dropwise to 200 ml of acetone. The resulting white precipitate was separated from the mother liquor using a sintered glass suction filter, washed with acetone and dried in a nitrogen current.

Similarly, the same amount of pyruvic acid and 0.21 g of citric acid were dissolved in 88 g of deionized water and further treated as above.

Both products were stored at room temperature and analyzed regularly. The course of by-product formation is shown in the following table.

| Without additions | | With addition of citric acid | |
|---|---|---|---|
| Storage period in days | Content of acyclic dimers (% hplc) | Storage period in days | Content of acyclic dimers (% hplc) |
| 0 | 0.9 | 0 | 0.3 |
| 1 | 1.2 | 1 | 0.4 |
| 5 | 2.1 | 6 | 0.7 |
| 8 | 2.4 | | |
| 12 | 2.8 | 14 | 1.1 |
| 19 | 3.1 | | |
| 27 | 3.9 | 27 | 1.5 |

EXAMPLE 3

Increasing the product quality by complexing traces of catalytically active heavy metals using EDTA 16.8 g (0.05 mol) of pyruvic acid (26.2%) were dissolved in 75.6 g of deionized water and 22 ml (0.02 mol) of a 10% suspension of calcium carbonate having an iron content of 260 ppm in water were added. A clear yellowish solution was formed. After stirring for 1.5 hours at room temperature the calcium pyruvate solution was more than 1% dimerized. 200 ml of cold acetone were added. The resulting white precipitate was separated from the mother liquor by a filtering centrifuge. The moist product, after standing overnight, was dried at 40° C. in vacuo (10 mbar). 5.5 g of a light-yellowish product were obtained. The content of monomeric calcium pyruvate. 2.5 $H_2O$ was 90%, and the content of acyclic dimer was above 4%.

Similarly, the same amount of pyruvic acid was dissolved in water together with 0.014 g of ethylenediaminetetraacetic acid, disodium salt dihydrate, and the same amount of calcium carbonate suspension in water was added. A clear colorless solution was formed. After stirring for 1.5 hours at room temperature, the calcium pyruvate solution was 0.7% dimerized. The solution was further treated as above. 5.5 g of a pure white product were obtained. The content of monomeric calcium pyruvate 2.5 $H_2O$ was 97%, and the content of acyclic dimer was 3%.

We claim:

1. A process for preparing high-purity calcium pyruvate or its hydrates by reacting an aqueous solution of pyruvic acid with an inorganic calcium compound with the pH being set to 2 to 7 which comprises reacting an up to 10% strength aqueous solution of pyruvic acid with the calcium compound, in the presence or absence of a stabilizer or complexing agent, and mixing the resulting solution With an organic diluent at temperatures of 0° to 30° C. and isolating the resulting precipitate of calcium pyruvate or its hydrate from the solution.

2. The process as claimed in claim 1, wherein a 1 to 8% strength aqueous solution of pyruvic acid is used.

3. The process as claimed in claim 1, wherein the reaction is carried out in the presence of a complexing agent for masking impurities due to heavy metals traces.

4. The process as claimed in claim 3, wherein the complexing agent used is ethylenediaminetetraacetic acid or its salts.

5. The process as claimed in claim 1, wherein the reaction is carried out in the presence of an organic acid as stabilizer.

6. The process as claimed in claim 5, wherein the organic acid used is citric acid, ascorbic acid, tartaric acid, fumaric acid, oxalic acid or malic acid.

7. The process as claimed in claim 1, wherein the pH is set to 2.5 to 4.

* * * * *